United States Patent

Viera et al.

[11] Patent Number: 5,318,541
[45] Date of Patent: Jun. 7, 1994

[54] APPARATUS FOR CATHETER EXCHANGE IN VASCULAR DILITATION

[75] Inventors: Fernando M. Viera, Hialeah; Michael W. Calhoun, Fort Lauderdale, both of Fla.

[73] Assignee: Cordis Corporation, Miami Lakes, Fla.

[21] Appl. No.: 24,509

[22] Filed: Mar. 2, 1993

[51] Int. Cl.$^5$ .............................................. A61M 5/18
[52] U.S. Cl. ..................................... 604/159; 604/164
[58] Field of Search ................. 604/103, 93, 158–160, 604/164, 165, 264, 280

[56] References Cited

U.S. PATENT DOCUMENTS

| | | | |
|---|---|---|---|
| 3,835,854 | 9/1974 | Jewett | 604/160 |
| 3,838,688 | 10/1974 | May et al. | 604/159 |
| 4,729,384 | 3/1988 | Bazenot et al. | 604/103 |
| 5,084,010 | 1/1992 | Plaia et al. | 604/22 |

Primary Examiner—J. L. Kruter
Attorney, Agent, or Firm—Watts, Hoffmann, Fisher & Heinke

[57] ABSTRACT

A catheter exchange tool for use in vascular dilitation procedures comprising a tool couplable between a balloon catheter and a balloon guidewire. The tool is operated by a physician to exert a longitudinal force on the balloon catheter and, in response to the exertion of the force on the catheter, simultaneously exert an equal and opposite force on the balloon guidewire.

14 Claims, 2 Drawing Sheets

APPARATUS FOR CATHETER EXCHANGE IN VASCULAR DILITATION

BACKGROUND OF THE INVENTION

1. Field of the Invention

This invention relates generally to the field of apparatus for use in vascular dilitation procedures such as angioplasty. The invention relates more specifically to a small, hand-held apparatus for simplifying and facilitating exchange of balloon catheters on a balloon guidewire used in an angioplasty procedure.

2. Background Art

As an example, cardiac catheterization procedures are well known for diagnosis and therapy relating to lesions in the cardiovascular system. One such procedure is angioplasty, for eliminating or ameliorating vascular plaque blockage or constriction in vessels which carry the heart's blood supply. In an angioplasty procedure, an expandable balloon is introduced into the patient's arterial system and advanced until it is positioned in the region of the blockage or constriction. Once so positioned, the balloon is expanded by filling it with a liquid. In successful procedures, the expandable balloon presses outwardly against the walls of the artery and expands the artery to a degree to which the artery is either partially or totally re-opened to blood flow.

A typical angioplasty procedure, and components used in practicing the procedure, are now described.

Prior to initiating the angioplasty procedure, a guiding catheter is placed typically via the femoral artery into the aorta and its tip is advanced to the entrance of the coronary arteries which branch from the aorta. This entrance into the coronary arteries is called the "osteum". Once placed, the guiding catheter acts as a conduit to access the coronary arteries with a balloon guidewire and balloon catheter. The guiding catheter is a portion of plastic tubing having a length of about 95 centimeters, an inside diameter of about 0.08 inches, and an outside diameter of about 2.5 millimeters.

The physician threads a balloon catheter onto a balloon guidewire. This operation takes place external to the patient.

The balloon guidewire is a piece of stainless steel and platinum wire, approximately 175 centimeters in length, and about 0.010–0.018 inches in diameter. The soft distal tip of the guidewire can be shaped to form a "J" configuration. This "J" shape allows the physician to steer the wire by twisting the proximal extremity of the wire while advancing or retracting the wire.

The balloon catheter is an elongated flexible plastic member defining two longitudinal passages and having a balloon located near its distal end. One longitudinal passage defines a sleeve through which the balloon guidewire can be passed. The other longitudinal passage defines a conduit communicating with the interior of the balloon and through which inflation fluid can be injected to inflate the balloon. The passage defining the sleeve for accommodating a guidewire is often called the "guidewire lumen". The passage defining the conduit for inflation fluid is often called the "inflation lumen".

Among the types of balloon catheters is one of a type in which the two longitudinal passages are generally side by side and parallel. In another type of balloon catheter, the two longitudinal passages are co-axial. In this latter type, the balloon guidewire is passed down the inner passage and the inflation fluid is injected into the balloon via the outer passage.

Balloon catheters, as well as associated apparatus and method for use in angioplasty, are described in U.S. Pat. No. 5,040,548, issued on Aug. 20, 1991, to Yock, and U.S. Pat. No. 4,762,129, issued on Aug. 8, 1988. Each of these issued U.S. patents is hereby expressly incorporated by reference.

The physician passes the balloon guidewire through the appropriate one of the longitudinal passages in the balloon catheter, leaving a portion of the balloon guidewire extending from the distal end of the balloon catheter and also a portion extending from its proximal end.

This assembly is then inserted into the proximal end of the guiding catheter, distal end first. The assembly is inserted until the balloon which is attached near the distal end of the balloon catheter is near the distal end of the guiding catheter. At this point, the physician, while maintaining the balloon catheter stationary, pushes on the balloon guidewire to advance it outwardly from the distal end of the guiding catheter.

The balloon guidewire can be steered by appropriate twisting movement by the physician.

The physician steers the balloon guidewire into the chosen one of the coronary arteries, and advances it until it reaches a location of constriction which the physician desires to re-open. Carefully, the physician eases the balloon guidewire through the region of restriction until a portion of the balloon guidewire is beyond the constriction, relative to the guiding catheter.

With the balloon guidewire held stationary, the physician then advances the balloon catheter. The distal end of the balloon catheter, as it is advanced, will, of course, follow the balloon guidewire which is already in place.

The physician continues to advance the balloon until it is located in the region of constriction of the artery. With the balloon and its associated catheter held stationary, inflation fluid is injected into the conduit which communicates with the balloon, causing it to inflate. Inflation of the balloon expands the walls of the artery in the region of constriction and, in successful procedures, re-opens the artery to sufficient blood flow.

Arteries vary in size, and therefore balloon catheters having balloons of different sizes are provided for the physician's selection. These balloons, when inflated, range from about 1.5 millimeters to about 4 millimeters in diameter.

Sometimes, it is necessary for the physician to use more than one balloon to open an artery. Sometimes, the chosen balloon is too large to be advanced into the constricted area. In other instances, the first chosen balloon size, even when inflated, is not large enough to open the constricted area to the degree desired. In such cases, it is necessary to exchange one balloon for another during the same angioplasty procedure.

In order to accomplish this exchange, the balloon guidewire is left in place, and the balloon catheter is withdrawn entirely from the guiding catheter until it is completely disengaged from the balloon guidewire. A new balloon catheter, having a different sized balloon, is then re-inserted over the balloon guidewire and advanced back to the location of the constricted area, where it is used to effect the desired result.

Once the balloon guidewire is initially in place, extending past the constricted area, it is highly desirable to leave the balloon guidewire in place for the entire remainder of the angioplasty procedure. This means that the balloon guidewire must remain in place even during exchanges of balloons. The reason for this is that, when a foreign object, such as the balloon guidewire, is introduced into an artery, the artery walls sometimes go into spasm, and constrict generally along a substantial portion of its length. If the artery tends to contract in this way, removal of the balloon guidewire while the artery is so contracted will sometimes render it virtually impossible to reinsert the guidewire through the contracted artery.

Withdrawal of the balloon catheter, while preventing movement of the balloon guidewire, is a difficult and cumbersome procedure. This procedure requires both a second individual, in addition to the physician, and the attachment of a removable extension to the proximal end of the guidewire.

In the catheter exchange procedure, removal of the catheter, and the insertion of the new catheter, is done manually. This is a two-hand operation for the physician. In addition, an attendant must hold the balloon guidewire longitudinally fixed with respect to the patient during the catheter exchange procedure.

Holding the balloon guidewire longitudinally fixed has been a difficult task. One reason for this is that, when the catheter to be removed is being slid proximally along the guidewire, friction between the balloon catheter and the balloon guidewire tends to dislodge the balloon catheter and move it in the proximal direction. As pointed out above, it is undesirable that the balloon guidewire move longitudinally during the exchange operation.

When a new catheter is being threaded upon an indwelling balloon guidewire, frictional forces tend to be generated which urge the balloon guidewire toward longitudinal movement in the distal direction. This, too, is undesirable.

It is a general object of this invention to provide an apparatus for simplifying and otherwise facilitating the catheter exchange operation in an angioplasty procedure, and to inhibit longitudinal motion of the balloon guidewire during the exchange procedure.

DISCLOSURE OF THE INVENTION

The disadvantages of the prior art are reduced or eliminated by a catheter exchange tool for use in vascular dilitation procedures, including apparatus couplable between a balloon catheter and a balloon guidewire, the apparatus being responsive to the application of motive power for exerting a longitudinal force on the balloon catheter and, in response to the exertion of the force on the balloon catheter, simultaneously exerting a substantially equal and opposite force on the balloon guidewire, when the balloon catheter is threaded onto the balloon guidewire.

This generation of equal and opposite forces on the guidewire and catheter reduces the likelihood that extension or retraction of the balloon catheter onto or off the balloon guidewire will exert undesirable forces on the balloon guidewire tending to dislodge and move it during a vascular dilitation procedure.

According to a more specific aspect, the apparatus includes further apparatus for removably engaging the catheter while the catheter is at least partially threaded onto the balloon guidewire. This removability feature facilitates removal of one catheter from a device and the attachment thereto of another catheter for exchange.

In a more specific embodiment, a power drive apparatus is added for applying the forces referred to above.

The power drive apparatus can comprise an electric motor, and electrical switching circuitry. The electrical switching circuitry can optimally be connected to a foot switch so that a physician using this catheter exchange device can actuate the device without the use of hands.

A specific embodiment of such a device includes a main body having structure for defining a passage for a guidewire extending through the main body along a particular path. The device also includes a connector mounted on the main body for removably engaging a catheter threaded onto a guidewire which is disposed along the path through the main body. Further, the apparatus includes means for frictionally engaging a guidewire disposed along the path for urging relative longitudinal motion between the guidewire and the main body.

According to a more specific aspect, the removable connector includes a Luer fitting.

Optionally, a rotatable adaptor can be coupled to the connector to afford free rotational movement between the main body and the catheter.

Also according to a specific embodiment, the means for exerting the relevant forces comprises a friction wheel engaged with the guidewire. This frictional engagement with the guidewire can be aided by the use of a guidewire support member which is mounted opposite the friction wheel with respect to the guidewire extending along the path, so that the guidewire support member impinges the guidewire against the outer surface of the friction wheel.

According to a more specific aspect, the outer surface of the friction wheel can be knurled.

The present invention will be understood in more detail by reference to the following specific descriptions, and to the drawings in which:

BEST MODE FOR CARRYING OUT THE INVENTION

Figure 1:
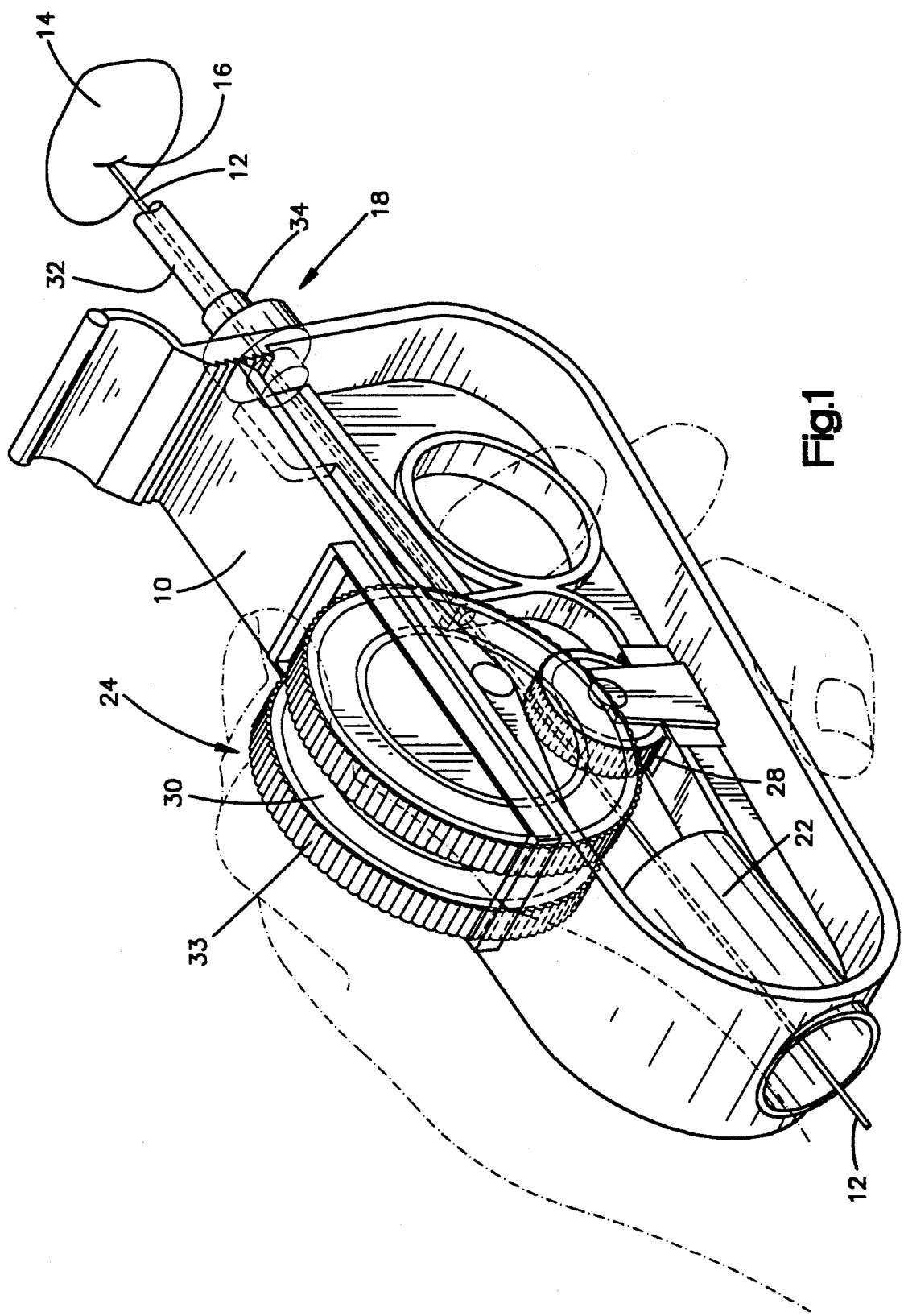
FIG. 1 is a perspective view of an apparatus embodying the present invention.
Figure 2:
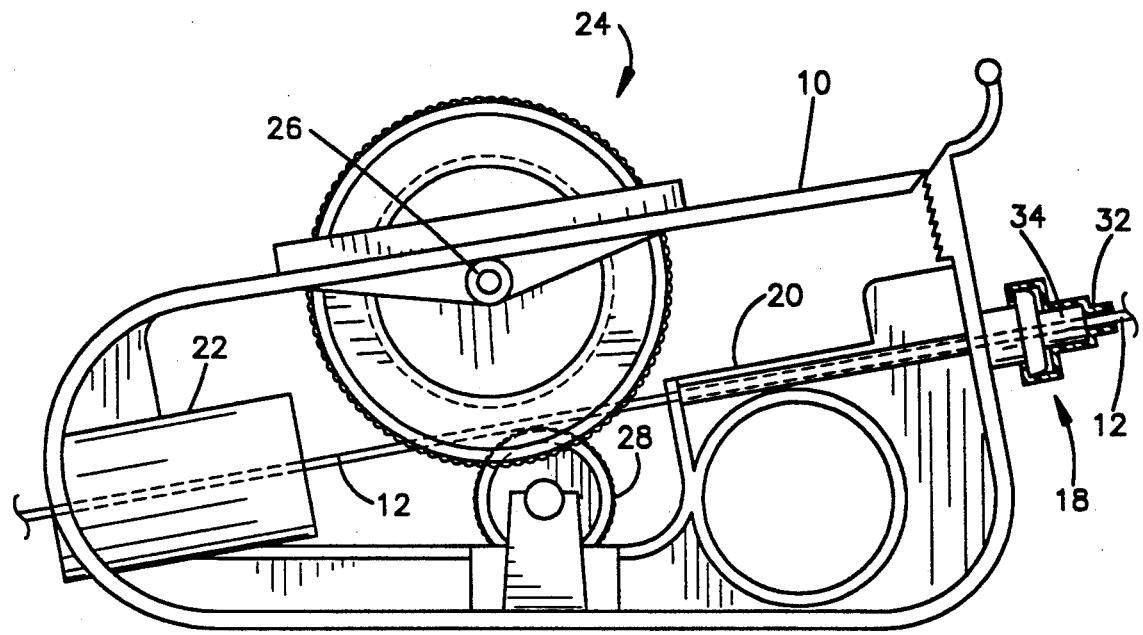
FIG. 2 is a side elevational view of an apparatus embodying the present invention.
Figure 3:
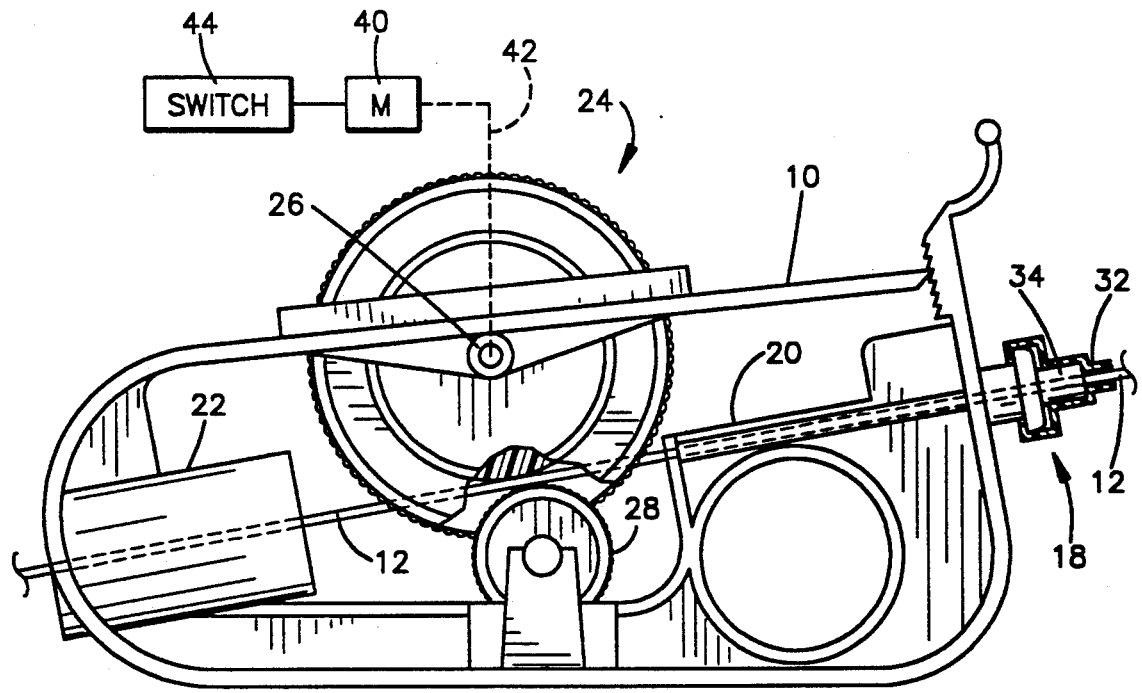
FIG. 3 is a side elevational view, partially broken-away, illustrating a detail of the apparatus of FIG. 2.

FIGS. 1-3 illustrate an embodiment of an apparatus for facilitating catheter exchange in a vascular dilitation procedure. The apparatus applies a longitudinal force to a balloon catheter which is threaded onto a balloon guidewire, and simultaneously exerts a substantially equal and opposite force on the balloon guidewire.

The apparatus includes a main body 10. The main body 10 includes structure for defining a path through the main body for a balloon guidewire 12. The balloon guidewire 12 is illustrated in FIG. 1 as entering a patient's body portion, illustrated generally at 14, through an incision 16.

The balloon guidewire 12 enters the right hand end of the main body through a fitting generally indicated at reference character 18. The main body also defines a tubular portion 20 through which the balloon guidewire passes, after entering the main body from the right hand side as illustrated in FIGS. 2 and 3. The tubular portion 20 has an inside diameter which is slightly larger than the outside diameter of the balloon guidewire.

The path of the balloon guidewire through the main body 10, from right to left, is further defined, near the left hand end of the main body, by another tubular portion 22, having an inside diameter considerably larger than the inside diameter of the tubular portion 20. The balloon guidewire 12 exits the left hand end of the main body 10 by way of the tubular portion 22.

Accordingly, a generally horizontal path for the balloon guidewire is defined from right to left through the main body 10, as illustrated in FIGS. 2 and 3.

A friction wheel 24 is mounted on the main body. The friction wheel 24 is journaled at 26 to the main body 10 for rotation about an axis substantially perpendicular to the plane of the paper in FIGS. 2 and 3. Thus, the axis of rotation of the friction wheel 24 is substantially perpendicular to the axis of the balloon guidewire 12 as it extends along its substantially horizontal path through the main body 10.

The friction wheel 24 is located such that its point of closest approach to the guidewire 12 is substantially adjacent the guidewire as it passes along its path through the main body 10. The wheel impinges against the guidewire.

A guidewire support 28 is also mounted on the main body. The guidewire support 28 is positioned such that it impinges from below on the guidewire 12 as it extends along its path through the main body, pressing the guidewire 12 into firm contact with the friction wheel 24. The friction wheel 24 defines a circumferential groove 30 in its outer surface. The action of the impingement of the guidewire support member 28 forces the guidewire 12 into snug frictional contact with the interior of the groove 30 of the friction wheel 24.

In a preferred embodiment, the interior of the groove 30 comprises a material having a relatively high coefficient of friction. Additionally, in the preferred embodiment, the exterior circumferential surface of the friction wheel, as at 33, is knurled. The purpose of the knurling is to facilitate manual rotation of the friction wheel 24.

It will be seen from the foregoing description that manual rotation of the friction wheel 24 will exert a longitudinal force on the balloon guidewire 12 as it extends along its defined path through the main body. If the friction wheel 24 is rotated in a clockwise direction, as shown in FIGS. 2 and 3, the balloon guidewire 12 will experience a longitudinal force tending to move the guidewire 12 toward the left in FIGS. 2 and 3. If the friction wheel 24 is rotated in a counter-clockwise direction, a force will be applied to the guidewire 12 which will tend to move it to the right. These conditions assume that the main body 10 is held in a substantially fixed position during rotation of the friction wheel 24.

A balloon catheter 32 is threaded over the balloon guidewire 12. The balloon catheter 32 can be inserted into the patient's body, guided by the balloon guidewire 12. The function of the balloon catheter 32 is described in detail in the preceding background section of this document.

The proximal end of the balloon catheter 32 is removably attached to the right hand end of a Luer fitting 34. In addition, a rotatable adaptor can also be added, such that the catheter 32 and the main body 10 can freely rotate relative to one another.

When the balloon guidewire 12 is disposed along its path through the main body 10, and the proximal end of the balloon catheter is removably attached to the right hand end of the main body 10, rotation of the friction wheel 24 causes relative longitudinal movement between the catheter 32 and the guidewire 12. For example, when the friction wheel 24 is rotated in a clockwise direction as shown in FIGS. 2 and 3, and the main body 10 held stationary, the balloon catheter 32 experiences a longitudinal force to the right as shown in FIGS. 2 and 3. This rightward exerted force tends to advance the balloon catheter 32 toward the right along the balloon guidewire, causing the balloon catheter to advance further into the patient's body. At the same time as the friction wheel 24 is rotated in the clockwise direction, applying a rightward force to the balloon catheter, a leftward extending longitudinal force is applied to the balloon guidewire. The leftward force exerted on the balloon guidewire is substantially equal and opposite to the rightward force exerted on the catheter.

This phenomenon is of great importance. In the prior art method of threading the balloon catheter manually to the right over the balloon guidewire, frictional forces between the guidewire and the balloon catheter 32 also cause the balloon guidewire to experience a force tending to extend the balloon guidewire into the body. It is not desirable that the balloon guidewire be moved during a vascular dilitation procedure such as angioplasty. The manual force, however, tending to advance the balloon guidewire in the same direction as that in which the balloon catheter is advanced, is a significant disadvantage, since this force on the balloon guidewire can cause it to move undesirably during advancement of the balloon catheter into the patient's body.

The device of the present invention reduces or eliminates this problem, by applying, in response to the advancing force on the balloon catheter, a substantially equal and opposite retracting force on the guidewire.

If the friction wheel 24 is rotated in the counter-clockwise direction, as illustrated in FIGS. 2 and 3, the action and reaction is opposite that which occurs if the friction wheel is rotated in a clockwise direction. That is, when the friction wheel 24 is rotated in a counter-clockwise direction, a retracting force, i.e., toward the left as shown in FIGS. 2 and 3, is exerted on the balloon catheter 32, while a simultaneous, substantially equal and opposite advancing force, is applied to the balloon guidewire 12. This equal and opposite force applied to the balloon guidewire 12 reduces the possibility that frictional contact between the interior of the balloon catheter and the outer surface of the balloon guidewire will result in the undesirable dislodgement of the balloon guidewire during withdrawal of the balloon catheter from the patient's body.

By the use of this device, the physician performing the vascular dilitation procedure can insert and withdraw balloon catheters both onto and from the balloon guidewire with greater speed and facility, and with the use of only one hand. In use, the physician holds the main body in one hand, and operates the friction wheel 24 with the thumb, as desired. The Luer fitting, which removably attaches the proximal end of the balloon catheter to the main body, is operated to release the balloon catheter after it has been entirely withdrawn from the patient's body, and facilitates the mounting of a new, different sized, catheter on the main body for subsequent advancement along the balloon guidewire and insertion into the patient's body.

It should be kept in mind that, as in all such procedures, an ample length of balloon guidewire extends leftward from the main body 10. This permits the travel of the device in the leftward direction along the unused portion of balloon guidewire extending from the patient's body, such that the balloon catheter 32 can be entirely withdrawn from the patient's body before the main body 10 reaches the proximal end of the balloon guidewire.

In a preferred embodiment, the guidewire support structure 28 is integrally formed as a part of the main body.

Optionally, power drive apparatus can be coupled to the friction wheel 24 to effect powered operation to advance and retract the balloon catheter. The power drive apparatus can be embodied by a small electric motor having the capability for operation in two directions. Such an electric motor is indicated in block form at reference character 40. Coupling means of known variety, indicated by a dotted line 42, couples the electric motor to the friction wheel 24.

The electric motor can be controlled by electrical switching circuitry of known type, indicated in block form at reference character 44. Preferably, a foot switch is provided to control the direction of operation of the electric motor 40. Also preferably, the electric motor can be of a variable speed variety, and the electrical switching circuitry can be of a type in which the degree of depression of the foot switch can control the speed of operation of the motor.

While the present invention has been described herein in some degree of particularity, it is to be understood that those of ordinary skill in the art may make certain additions or modifications to, or deletions from, the described present embodiment of the invention without departing from the spirit or the scope of the invention, as set forth in the appended claims.

We claim:

1. An apparatus for facilitating catheter exchange in a vascular dilitation procedure wherein a catheter slideably overlying a portion of a catheter guidewire is removed and replaced while at least a distal portion of the guidewire remains within a body of a patient, said apparatus comprising:
   a) a main body defining structure for facilitating passage of a catheter guidewire through said main body along a path;
   b) a catheter engaging means for removably engaging a proximal end of the catheter;
   c) drive means supported by the main body for frictionally engaging an exposed portion of the guidewire passing through the main body and adapted to convert an application of motive power into longitudinal movement of the main body, and a catheter attached to the catheter engaging means, along the guidewire.

2. The apparatus of claim 1, wherein said catheter engaging means comprises a luer fitting.

3. The apparatus of claim 1, further comprising:
   a rotatable adaptor coupled to said catheter engaging means.

4. The apparatus of claim 1, wherein driving means comprises a drive wheel rotatably mounted on said main body wherein the wheel frictionally engages the exposed portion of the guidewire passing through the main body.

5. The apparatus of claim 4, wherein said wheel is mounted for rotation about an axis substantially perpendicular to the axis of a guidewire disposed along said path.

6. The apparatus of claim 5, further comprising:
   a guidewire support member substantially adjacent said path near the point of closest approach of said wheel to said path.

7. The apparatus of claim 6, wherein said guidewire support member is integrally formed with said main body.

8. The apparatus of claim 4, wherein the outer periphery of said wheel is toothed.

9. The apparatus of claim 4, wherein said wheel defines a peripheral groove having therein a material having a relatively high coefficient of friction.

10. The apparatus of claim 4, further comprising:
    power means coupled to the drive means for rotating said wheel.

11. The apparatus of claim 10, wherein:
    said power means comprises an electric motor and a switching circuit adapted for selectively activating the electric motor.

12. The apparatus of claim 1, further comprising:
    power means for applying motive power to the drive means.

13. The apparatus of claim 12, wherein:
    said power means comprises an electric motor and a switching circuit adapted selectively activating the electric motor.

14. A method of removing a catheter overlying a guidewire during a vascular dilitation procedure using a catheter exchange tool wherein at least a distal portion of the guidewire remains in place in a patient during removal of the catheter, the exchange tool being removably attachable to a proximal end of the catheter and including a body portion through which the guidewire can pass, the exchange tool further including a drive means adapted to convert an application of motive power into longitudinal movement of the exchange tool, and the catheter attached thereto, along the guidewire, the method comprising the steps of:
    a) threading the body portion of the exchange tool onto the proximal end of the guidewire;
    b) moving the exchange tool along the guidewire into engagement with the proximal end of the catheter;
    c) attaching the exchange tool to the proximal end of the catheter;
    d) applying motive power to the drive means of the exchange tool so as to longitudinally move the exchange tool, and the catheter attached to the exchange tool, to the proximal end of the guidewire;
    e) removing the exchange tool from the proximal end and of guidewire;
    f) moving the exchange tool away from the proximal end of the guidewire until the catheter is separated from the guidewire; and
    g) detaching the exchange tool from the proximal end of the catheter.

* * * * *